(12) United States Patent
Hwang

(10) Patent No.: US 11,541,156 B2
(45) Date of Patent: Jan. 3, 2023

(54) BREAST PUMP ASSEMBLY

(71) Applicant: Hyo Soon Hwang, Yongin-Si (KR)

(72) Inventor: Hyo Soon Hwang, Yongin-Si (KR)

( * ) Notice: Subject to any disclaimer, the term of this patent is extended or adjusted under 35 U.S.C. 154(b) by 0 days.

(21) Appl. No.: 17/644,258

(22) Filed: Dec. 14, 2021

(65) Prior Publication Data

US 2022/0265907 A1    Aug. 25, 2022

(30) Foreign Application Priority Data

Feb. 22, 2021    (KR) .......................... 10-2021-0023050

(51) Int. Cl.
*A61M 1/06*    (2006.01)

(52) U.S. Cl.
CPC ............ *A61M 1/064* (2014.02); *A61M 1/067* (2021.05)

(58) Field of Classification Search
CPC .............................................. A61M 1/06–069
See application file for complete search history.

(56) References Cited

U.S. PATENT DOCUMENTS

| 11,090,418 B2 | 8/2021 | Hwang |
| 2018/0028732 A1 * | 2/2018 | Rigert ...................... A61M 1/06 |

FOREIGN PATENT DOCUMENTS

| KR | 1020180076538 | 7/2018 |
| KR | 1020190116774 | 10/2019 |

OTHER PUBLICATIONS

Office Action issued in KR10-2021-0023050, dated Apr. 30, 2021.

* cited by examiner

*Primary Examiner* — Nathan R Price
*Assistant Examiner* — Courtney B Fredrickson
(74) *Attorney, Agent, or Firm* — Grossman, Tucker, Perreault & Pfleger, PLLC

(57) ABSTRACT

A breast pump assembly is disclosed. The breast pump assembly according to an aspect of the present disclosure may include: a breast pump including a contact housing with a backside recessed to wrap a breast and a storage housing coupled to the contact housing to define a breast milk storage space on a frontside of the contact housing, the breast pump being provided with a coupling cavity penetrating an upper portion of the storage housing; a stopper detachably coupled to the coupling cavity and provided with a first air pipe connector; an air pipe coupled to the first air pipe connector; and a pump cradle provided with a second air pipe connector to which the air pipe is coupled, wherein the pump cradle includes: a first case provided with the second air pipe connector, an insertion hole and an air passage connector; a first milking pump installed in the first case; a duct connecting the first milking pump and the air passage connector to the second air pipe connector; and a pump module including a second case detachably coupled to the insertion hole and a second milking pump installed in the second case, wherein the second case is provided with an air passage connecting the air passage connector with the second milking pump, and wherein the pump module is separated from the insertion hole and detachably coupled to the coupling cavity from which the stopper is separated.

10 Claims, 16 Drawing Sheets

BREAST PUMP ASSEMBLY

BACKGROUND

1. Field

The present disclosure is related to a breast pump assembly, more specifically to a breast pump assembly that allows a hands-free use during extraction of breast milk.

2. Description of Related Art

The presently marketed breast pumps are either manually powered or electrically powered, depending on the type of power source.

The manual powered breast pump generally includes a suction unit being fitted over the breast, a manual pumping unit configured for creating an air pressure in the suction unit, and a bottle for storing the milk extracted through the suction unit. Such a breast pump has required a user to hold the suction unit or the bottle and manipulate the manual pumping unit while extracting the milk, thereby hindering the free use of the hands.

On the contrary, the electric powered breast pump uses an electric pump instead of the manual pumping unit to allow the free use of one hand, the user still has to use the remaining hand to hold the suction unit or the bottle.

Accordingly, the inventor of this disclosure has developed a motorized breast pump in which a contact housing, which makes a tight contact with the breast, and a storage housing, which stores the extracted milk, are coupled such that the breast pump may be inserted between the breast and a brassiere, as disclosed in KR Application Publication No. 10-2019-0116774. This breast pump is particularly characterized by generating air pressure through an attachable pump module, which may be detachably coupled to the storage housing, for an improved portability. Nonetheless, the attachable pump module suffers with a lower efficiency than an external pump module due to the limited pumping capacity caused by, for example, the restricted weight. This shortcoming is especially true when the breast pump is used at home or at any other place where the external pump module is readily available.

PRIOR ART DOCUMENTS

Patent Documents (Patent Document 1) KR Utility Model Registration No. 20-0469719 (Nov. 1, 2013, "Apparatus extracting mother's milk")
(Patent Document 2) KR Application Publication No. 10-2019-0116774 (Oct. 15, 2019, "Breast pump")

SUMMARY

A certain embodiment of the present disclosure provides a breast pump assembly that allows a free use of both hands while extracting milk and improves a portability but is capable of increasing a pumping capacity when necessary.

An aspect of the present disclosure may provide a breast pump assembly including: a breast pump including a contact housing with a backside recessed to wrap a breast and a storage housing coupled to the contact housing to define a breast milk storage space on a frontside of the contact housing, the breast pump being provided with a coupling cavity penetrating an upper portion of the storage housing; a stopper detachably coupled to the coupling cavity and including a first air pipe connector; an air pipe coupled to the first air pipe connector; and a pump cradle provided with a second air pipe connector to which the air pipe is coupled, wherein the pump cradle includes: a first case provided with the second air pipe connector, an insertion hole and an air passage connector; a first milking pump installed in the first case; a duct connecting the first milking pump and the air passage connector to the second air pipe connector; and a pump module including a second case detachably coupled to the insertion hole and a second milking pump installed in the second case, wherein the second case may be provided with an air passage connecting the air passage connector with the second milking pump, and wherein the pump module may be separated from the insertion hole and detachably coupled to the coupling cavity from which the stopper is separated.

The air passage may be connected to the coupling cavity when the pump module is coupled to the coupling cavity.

The pump cradle may further include: a first input unit; and a first control panel configured for driving the first milking pump and the second milking pump based on an actuating signal inputted through the first input unit.

The second milking pump may be connected to the first control panel through a Universal Serial Bus (USB) plug and a USB socket provided in the first case and the second case and detachably coupled with each other.

The pump module may further include: a second input unit; and a second control panel configured for driving the second milking pump based on an actuating signal inputted through the second input unit.

The first input unit may be coupled to the first case, and the second input unit may be coupled to the second case.

The pump cradle may further include a sealing cap, which may be detachably coupled to the air passage connector that is separated from the air passage, and the first case may be provided with a receiving hole to which the sealing cap is detachably coupled after separating from the air passage connector.

The contact housing may be provided with a protruding part formed at a portion corresponding to a nipple and extending toward a front, and the breast pump may further include: a cap connector coupled to the protruding part and forming a first inner space connected to the backside; a funnel connector coupled to the cap connector and forming a second inner space connected to the first inner space; and a flow separation membrane configured to separate the second inner space from the coupling cavity.

The cap connector may be provided with a breast milk outflow tube connecting the first inner space with the breast milk storage space.

Another aspect of the present disclosure may provide a pump cradle for a breast pump, including: a first case provided with an air pipe connector, an insertion hole and an air passage connector, the air pipe connector connected to the breast pump through an air pipe; a first milking pump installed in the first case; a duct connecting the first milking pump and the air passage connector to the air pipe connector; and a pump module including a second case detachably coupled to the insertion hole and a second milking pump installed in the second case, wherein the second case is provided with an air passage connecting the air passage connector with the second milking pump, and wherein the pump module may be separated from the insertion hole and detachably coupled to the breast pump.

According to a certain embodiment of the present disclosure, the breast pump with the storage housing coupled to the contact housing may be inserted between the breast and the brassiere, thereby allowing for free use of both hands while extracting milk.

Moreover, the pump module may be directly coupled to the breast pump for an improved portability, and the pump module may be coupled to the pump cradle for an increased pumping capacity.

DETAILED DESCRIPTION

Hereinafter, a certain preferred embodiment of the present disclosure will be described with reference to the accompanying drawings. Unless clearly defined otherwise, the terms used in describing the embodiment of the present disclosure may be interpreted to meanings generally perceived by those who are ordinarily skilled in the art to which the present disclosure pertains, shall be deemed to simply describe a certain embodiment, and shall by no means restrict the present disclosure.

Unless specifically described, a singular form shall be construed to include a plural form. When a certain portion is described to "comprise," "consist of" or "include" certain element(s), said certain portion shall be construed to include other element(s) as well. Moreover, when something is described to be "on" an element, it shall be interpreted that said something is above or below said element and not necessarily at an upper side in the gravitational direction. Moreover, when an element is described to be "connected" or "coupled" to another element, not only shall it mean that said element is directly connected or coupled to the other element, but it shall also mean said element is indirectly connected or coupled to the other element via a different element. While terms such as "first" and "second" may be used in describing a certain element, such terms are used to distinguish said certain element from other elements and shall by no means restrict said certain element to a characteristic, order or sequence.

Figure 1:
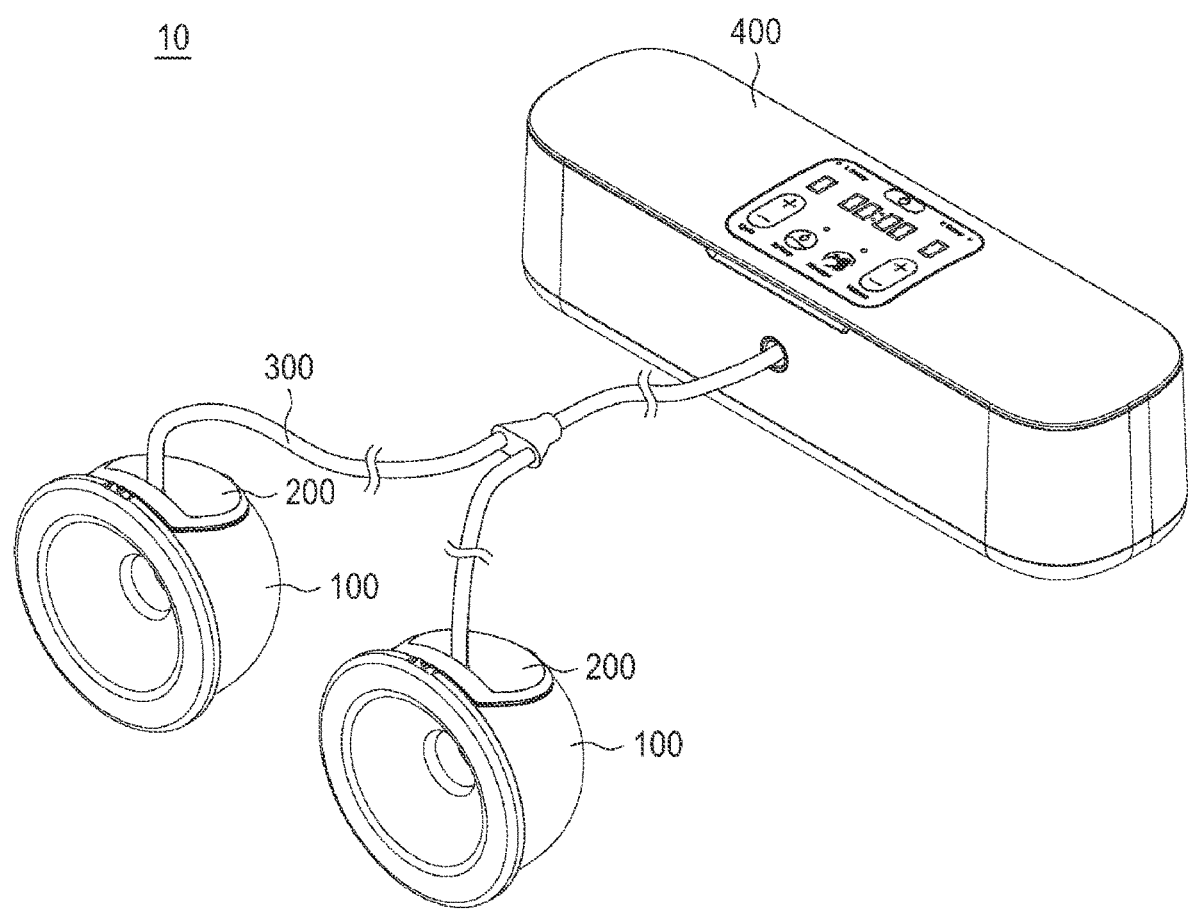
FIG. 1 is a perspective view illustrating a breast pump assembly according to an embodiment of the present disclosure.
Figure 2:
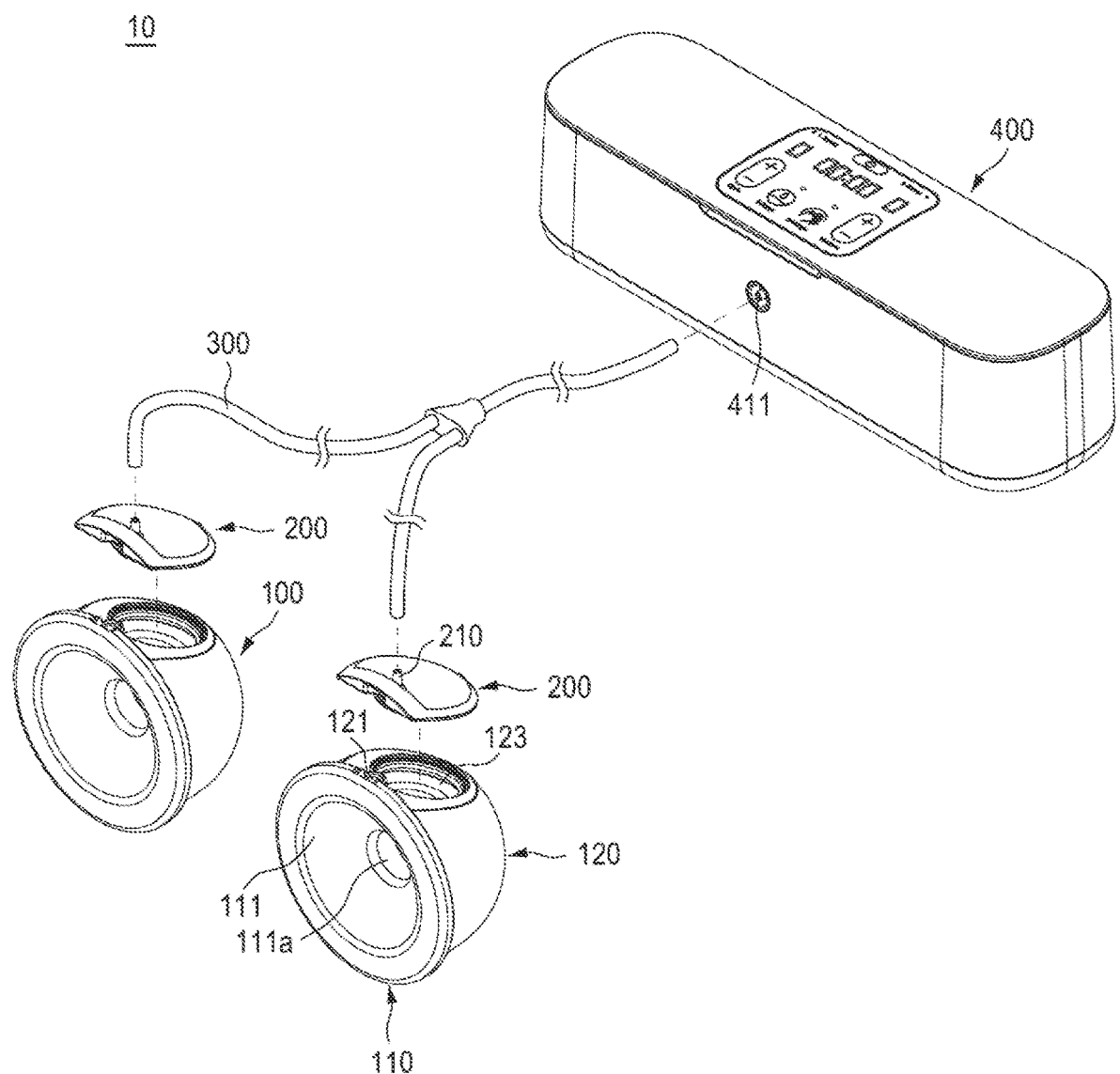
FIG. 2 is an exploded view of the breast pump assembly shown in FIG. 1.

FIG. 1 is a perspective view illustrating a breast pump assembly in accordance with an embodiment of the present disclosure, and FIG. 2 is an exploded perspective view of the breast pump assembly shown in FIG. 1. Referring to FIG. 1 and FIG. 2, the breast pump assembly 10 in accordance with an embodiment of the present disclosure may include a breast pump 100, a stopper 200, an air pipe 300 and a pump cradle 400.

The breast pump 100 may include a contact housing 110 and a storage housing 120. The contact housing 110 may have a backside 111 recessed to wrap a breast. A breast milk inflow cavity 111a may be formed at a portion of the backside corresponding to a nipple of the breast. The storage housing 120 may be coupled to the contact housing 10 to define a breast milk storage space on a frontside of the contact housing 110. The breast milk storage space may be connected to the breast milk inflow cavity 111a. For instance, the breast milk storage space may be in contact with the frontside of the contact housing 110, and the breast milk may be flowed in through the breast milk inflow cavity 111a and stored in the breast milk storage space. The storage housing 120 may be detachably coupled to the contact housing 110. Accordingly, a user may separate the storage housing 120 from the contact housing 110, after having extracted the breast milk, and transfer the breast milk stored in the breast milk storage space of the storage housing 120 to another container, such as, for example, a nursing bottle. The storage housing 10 may be additionally provided with a breast milk outflow cavity 121 connected to the breast milk storage space such that the breast milk stored in the breast milk storage space of the storage housing 120 may be transferred to another container without having to separate the storage housing 120 from the contact housing 110.

The breast milk outflow cavity 121 may penetrate an upper portion of the storage housing 120 and may have an overflow preventing cap (not shown) detachably coupled thereto. The storage housing 120 may be also provided with a coupling cavity 123 penetrating the upper portion of the storage housing 120.

The stopper 200 may be detachably coupled to the coupling cavity 123 to close off an outlet of the coupling cavity 123. The stopper 200 may be provided with a first air pipe connector 210. The first air pipe connector 210 may be provided with a first flow channel connecting the coupling cavity 123 with an inner space of the air pipe 300. The air pipe 300 may be detachably coupled to the first air pipe connector 210 and may include, for example, a hose.

The air pipe 300 may include a Y-type splitter in case two breast pumps 100 are connected to a single pump cradle 400 to extract the breast milk simultaneously from both breasts of a lactating person. Nonetheless, the present disclosure is not limited to this configuration only, and it is possible that a single breast pump 100 is connected to a single pump cradle 400, in which case the Y-type splitter may be omitted.

The pump cradle 400 may be connected to the breast pump 100 via the air pipe 300 to provide an air suction force for extraction. To this end, the pump cradle 400 may be provided with a second air pipe connector 411 to which the air pipe 300 is coupled. The second air pipe connector 411 may be provided with a second flow channel connecting the inner space of the air pipe 300 with an inner space of a duct within the pump cradle 400.

Figure 3:
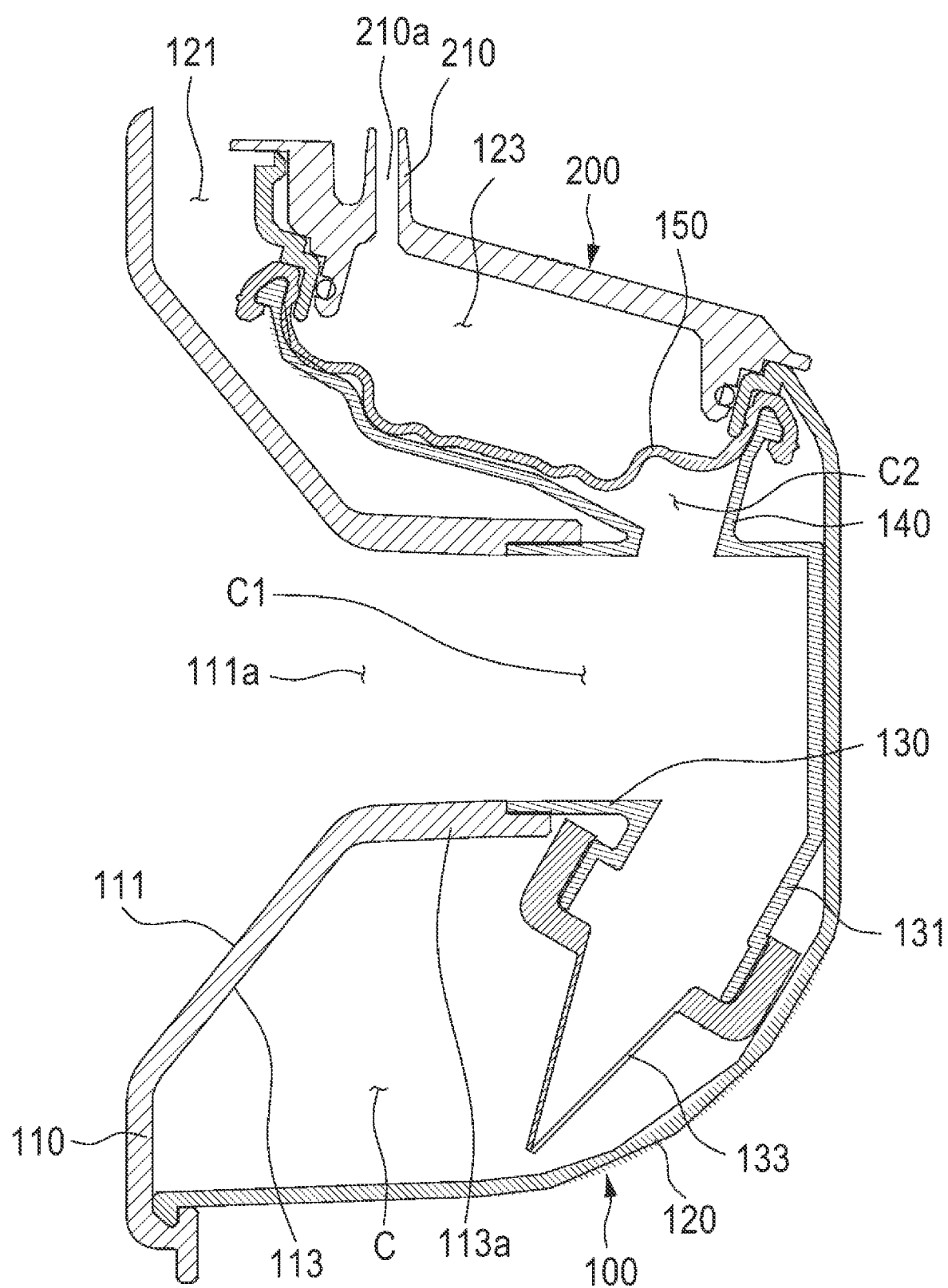
FIG. 3 is a cross-sectional view of the breast pump shown in FIG. 1.
Figure 4:
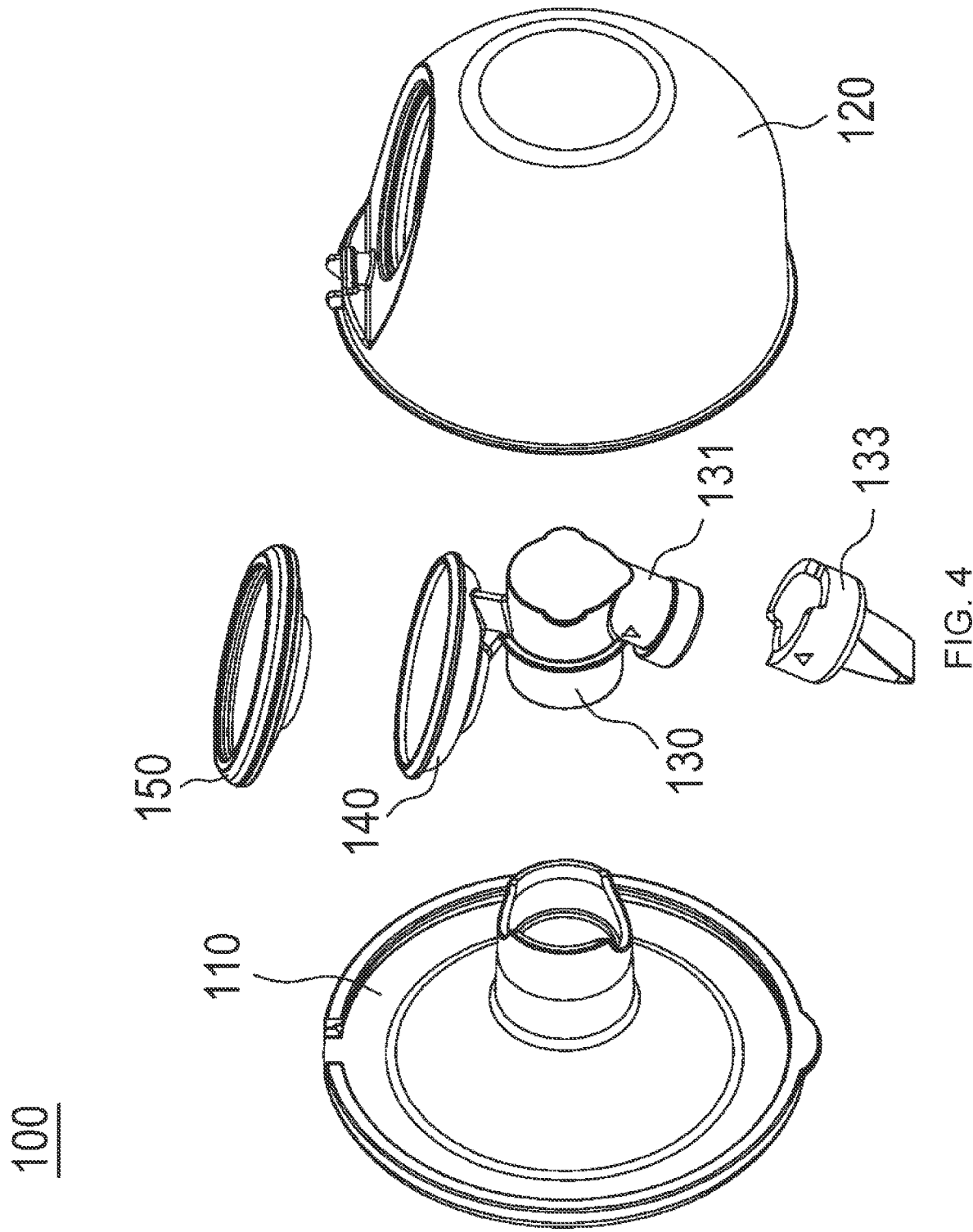
FIG. 4 is an exploded perspective view of the breast pump shown in FIG. 1.

FIG. 3 is a cross-sectional view of the breast pump shown in FIG. 1, and FIG. 4 is an exploded perspective view of the breast pump shown in FIG. 1. Referring to FIG. 3 and FIG. 4, the breast pump 100 may include the contact housing 110 and the storage housing 120, and may further include a cap connector 130, a funnel connector 140 and a flow separation membrane 150.

The contact housing 110 may be provided with a protruding part 113a formed at a portion of a frontside 113 of the contact housing 110 corresponding to a nipple of the lactating person and extending toward a front. The protruding part 113a may be in a pipe shape with both ends open, and a first end of the protruding part 113a may be connected to the breast milk inflow cavity 111a. Here, the frontside 113 may refer to an opposite face of the backside 111.

As described above, the storage housing 120 may be coupled to the contact housing 110 to form a breast milk storage space C on the frontside 113 of the contact housing. The cap connector 130 may be detachably coupled to a second end of the protruding part 113a to form a first inner space C1 connected to the backside 111 or breast milk inflow cavity 111a of the contact housing 110. The cap connector 130 may be provided with a breast milk outflow tube 131 connecting the first inner space C1 with the breast milk storage space C. The breast milk storage space C may be downwardly extended at a lower portion of the cap connector 130. Accordingly, the breast milk may flow in to the first inner space C1 through the breast milk inflow cavity 111a and then may be discharged, by its own weight, to the breast milk storage space C through the breast milk outflow tube 131.

The breast milk outflow tube 131 may have a silicon valve 133 coupled to a lower end thereof for inhibiting the breast milk from a back flow. Formed at a tip end of the silicon valve 133 may be a perforated line. Accordingly, the breast milk stored in the breast milk storage space C may hardly be flowed into the silicon valve 133 past the perforated line, but the breast milk flowed into the silicon valve 133 through the breast milk outflow tube 131 may be readily discharged to the breast milk storage space C by expanding the silicon valve 133 to open the perforated line.

The funnel connector 140 may be coupled to an upper portion of the cap connector 130 and form a second inner space C2 connected to the first inner space C1. For example, the second inner space C2 may be formed by a recessed upper face of the funnel connector 140.

A connection channel for connecting the first inner space C1 with the second inner space C2 may be formed between the cap connector 130 and the funnel connector 140, and the coupling cavity 123 may be formed at a portion of the storage housing 120 facing the second inner space C2 of the funnel connector 140. The funnel connector 140 may be manufactured separately from the cap connector 130 before being coupled to the cap connector 130, but the present disclosure is not limited to this configuration, and the funnel connector 140 may be integrally manufactured with the cap connector 130, as illustrated in the accompanying drawings.

The flow separation membrane 150 may separate the second inner space C2 from the coupling cavity 123. For example, the flow separation membrane 150 may be detachably coupled to the coupling cavity 123 and the funnel connector 140 to close off an entrance of the coupling cavity 12 and an upper face of the second inner space C2 simultaneously.

The flow separation membrane 150 may be a membrane form of member that may be made of a flexible material so as to be easily bent by a change of air pressure within the coupling cavity 123. Accordingly, once the air within the coupling cavity 123 is discharged through the first flow channel 210a provided in the first air pipe connector 210, the middle portion of the flow separation membrane 150 may move upwardly, thereby expanding the second inner space C2 to create a vacuum pressure within the second inner space C2, and this vacuum pressure may be extended to the first inner space C1 to act as a force for extracting the breast milk from the breast of the lactating person.

Moreover, since the second inner space C2 and the coupling cavity 123 are structured to be separated or isolated from each other by the flow separation membrane 150, the breast milk within the first inner space C1 is prevented from flowing to the milking pump even if the breast milk in the first inner space C1 flows into the second inner space C2, thereby preventing the milking pump from contamination or damage by the breast milk.

Figure 5:
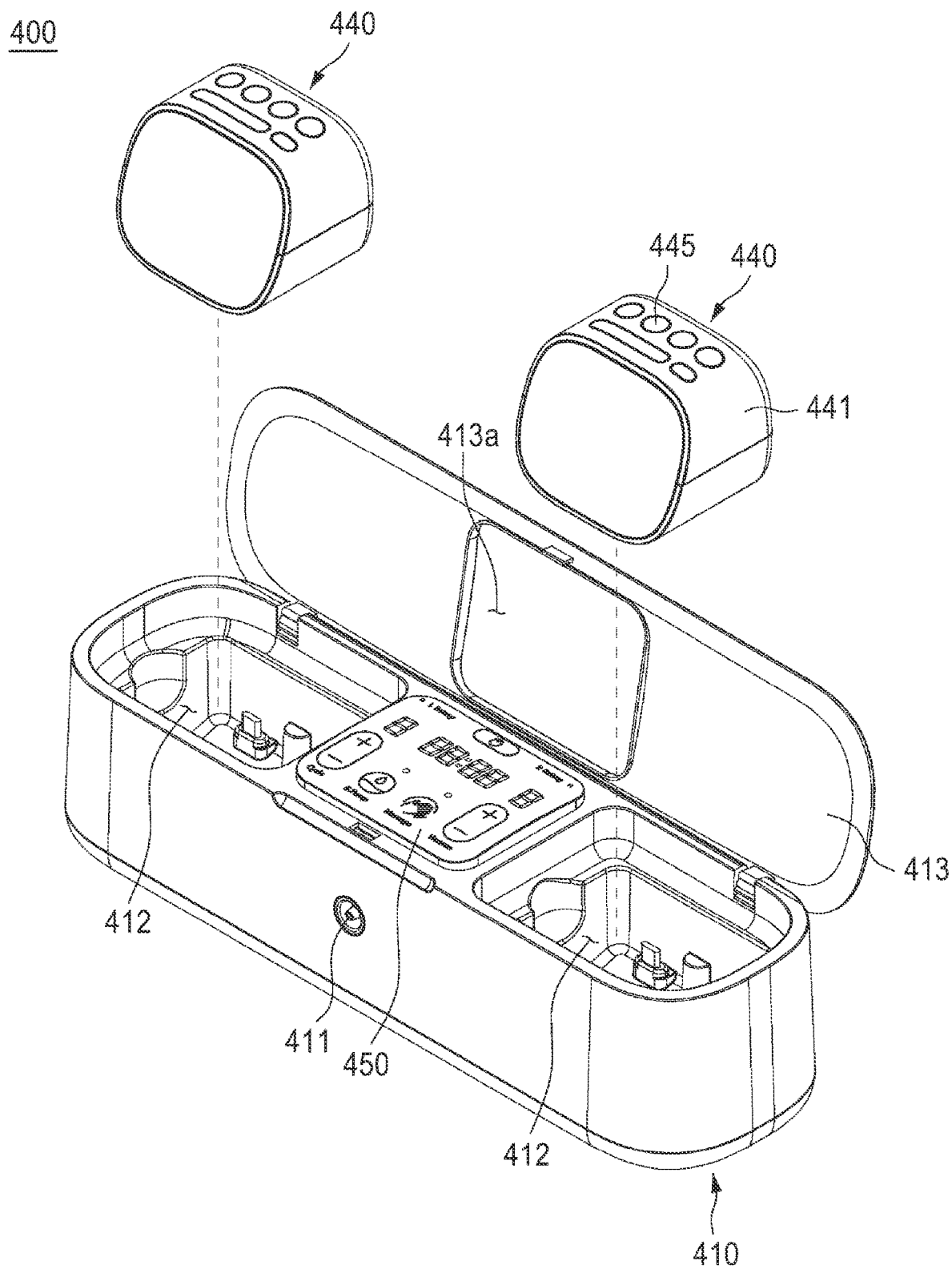
FIG. 5 is an exploded perspective view of the pump cradle shown in FIG. 2.
Figure 6:
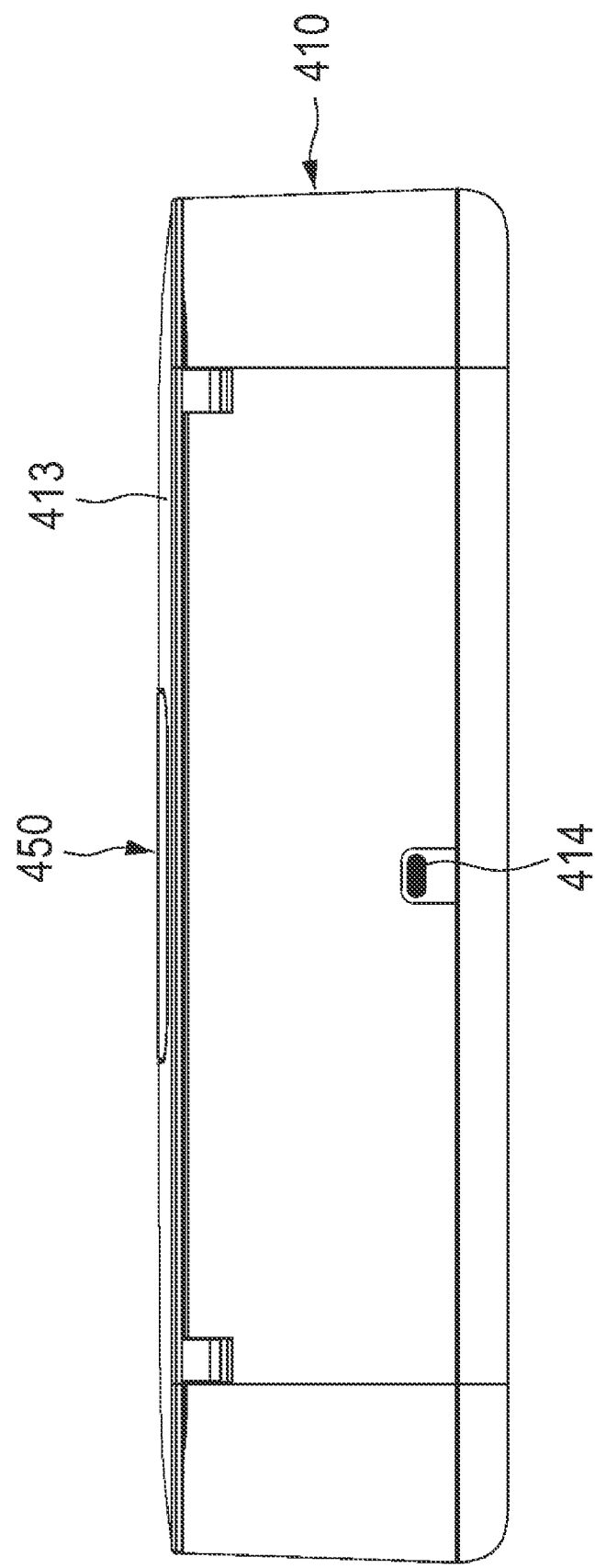
FIG. 6 is a rear view of the pump cradle shown in FIG. 5.
Figure 7:
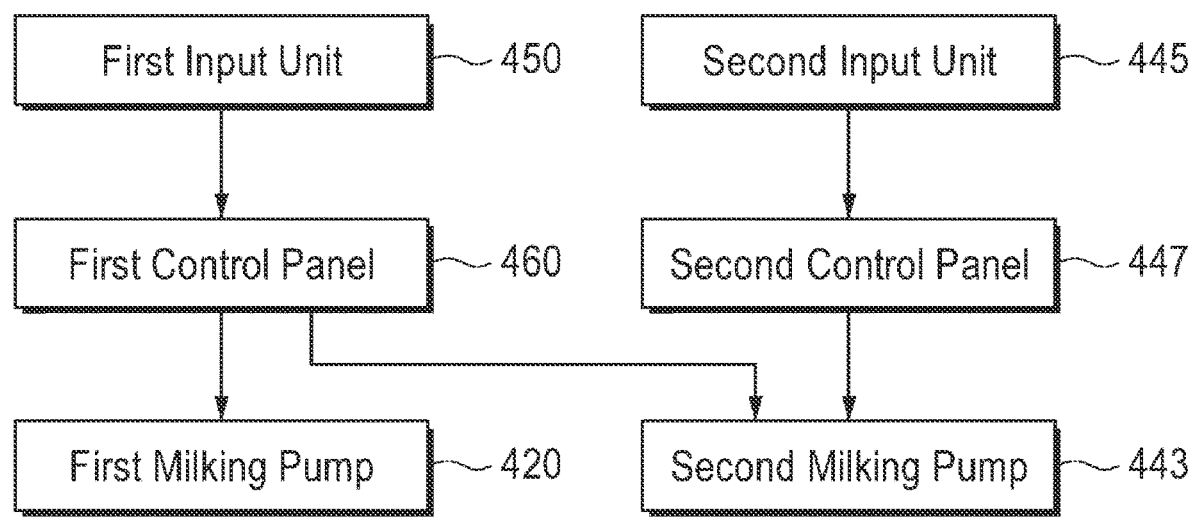
FIG. 7 is a block diagram for illustrating the control logic of the pump cradle shown in FIG. 5.

FIG. 5 is an exploded perspective view of the pump cradle shown in FIG. 2, and FIG. 6 is a rear view of the pump cradle shown in FIG. 5, and FIG. 7 is a block diagram for illustrating the control logic of the pump cradle shown in FIG. 5. Referring to FIG. 5 to FIG. 7, the pump cradle 400 may include a first case 410, a first milking pump 420 and a pump module 440 and may further include a first input unit 450 and/or a first control panel 460.

The first case 410 may be provided with the second air pipe connector 411 and an insertion hole 412 and may be further provided with a cover 413 and/or a power socket 414. The second air pipe connector 411 may be formed, for example, in a front face of the first case 410 and may have the air pipe 300 detachably coupled thereto, as described above. The insertion hole 412 may be formed, for example, on a top face of the first case 410 and may have the pump module 440 detachably coupled thereto. The first case 410 may have a pair of insertion holes 412 formed therein such that a pair of pump modules 440 separated from a pair of breast pumps 100 may be coupled, respectively, thereto, but the present disclosure is not necessarily limited to this configuration.

The cover 413 may be pivotally coupled to the body of the first case 410 to open and close the insertion hole 412. Moreover, the cover 413 may be provided with a through hole 413a at a location corresponding to the first input unit 450 such that the first input unit 450 formed on the top face of the first case 410 may be externally exposed even when the insertion hole 412 is closed by the cover 413.

The power socket 414 may be formed, for example, on a rear face of the first case 410 and may have a power plug (not shown) of an external power source (not shown) detachably coupled thereto.

The first milking pump 420 may be installed in the first case 410 and may include an electric pump for periodically generating an air suction force when electricity is supplied. The electricity required for driving the first milking pump 420 may be supplied from the external power source via the power socket 414. It shall be appreciated however that the source of electric power is not limited to the external power source. For example, the electricity may be supplied from a first battery (not shown) installed in the first case 410.

The pump module 440 may include a second case 441 and a second milking pump 443 and may further include a second input unit 445 and/or a second control panel 447. The second case 441 may be detachably coupled to the insertion hole 412 of the first case 410. Moreover, the second case 441 may be separated from the insertion hole 412 and detachably coupled to the coupling cavity 123 from which the stopper 200 is separated. As such, the pump module 440 may be used selectively with the pump module 440 directly coupled to the breast pump 100 or with the pump module 440 coupled to the first case 410 of the pump cradle 400.

The second milking pump 443 may be installed in the second case 441 and may include an electric pump for periodically generating an air suction force when electricity is supplied. The electricity required for driving the second milking pump 443 may be supplied from a second battery (not shown) installed in the second case 441.

The second input unit 445 may be coupled to the second case 441 such that the second input unit 445 is externally exposed and may have an actuating signal for driving the second milking pump 443 inputted thereto. For example, the user may input the actuating signal by use of, for example, buttons and a touch screen provided in the second input unit 445. Moreover, the second input unit 445 may include a first display panel for displaying an operation state of the pump module 440.

The second control panel 447 may be installed in the second case 441 and may drive the second milking pump 443 based on the actuating signal inputted through the second input unit 445. Accordingly, in the case where the pump module 440 is directly coupled to the breast pump 100, the user may drive the second milking pump 443 by inputting the actuating signal through the second input unit 445.

The first input unit 450 may be coupled to the first case 410 such that the first input unit 450 is externally exposed and may have an actuating signal for driving the first milking pump 420 and the second milking pump 443 inputted thereto. For instance, the user may input the actuating signal by use of, for example, buttons and a touch screen provided in the first input unit 450. Moreover, the first input unit 450 may include a second display panel for displaying an operation state of the pump cradle 400.

The first control panel 460 may be installed in the first case 410 and may drive the first milking pump 420 and the second milking pump 443 based on an actuating signal inputted through the first input unit 450. Accordingly, in the case where the pump module 440 is coupled to the first case 410 of the pump cradle 400, the user may drive the first milking pump 420 and the second milking pump 443 by inputting the actuating signal through the first input unit 450.

Meanwhile, the first milking pump 420 and the second milking pump 443 may each include a solenoid valve, and when the first milking pump 420 and the second milking pump 443 are driven by the first control panel 460, the solenoid valve may be activated in the first milking pump 420 only and may not be activated in the second milking pump 443.

Figure 8:
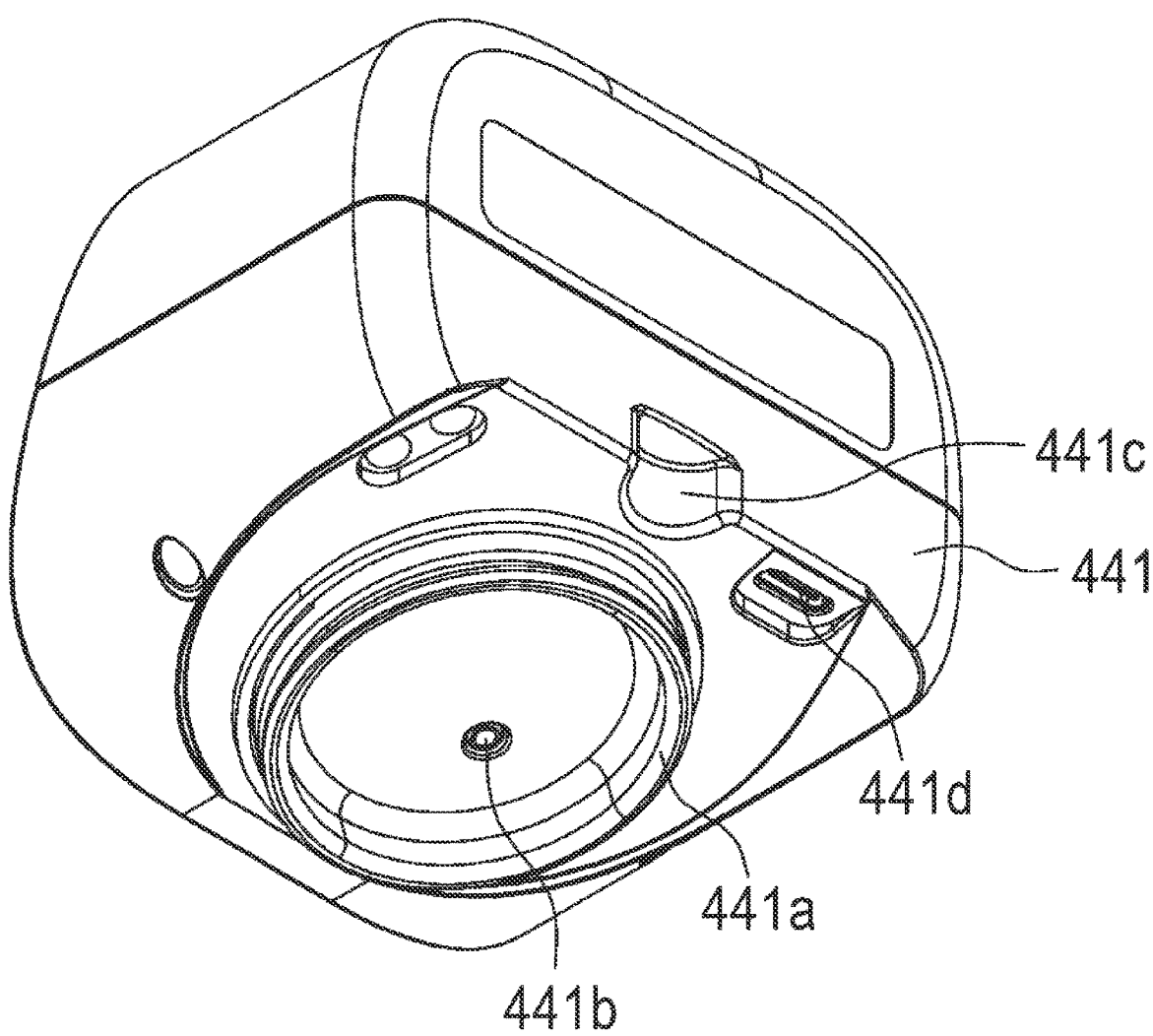
FIG. 8 is a perspective view of the pump module shown in FIG. 5.
Figure 9:
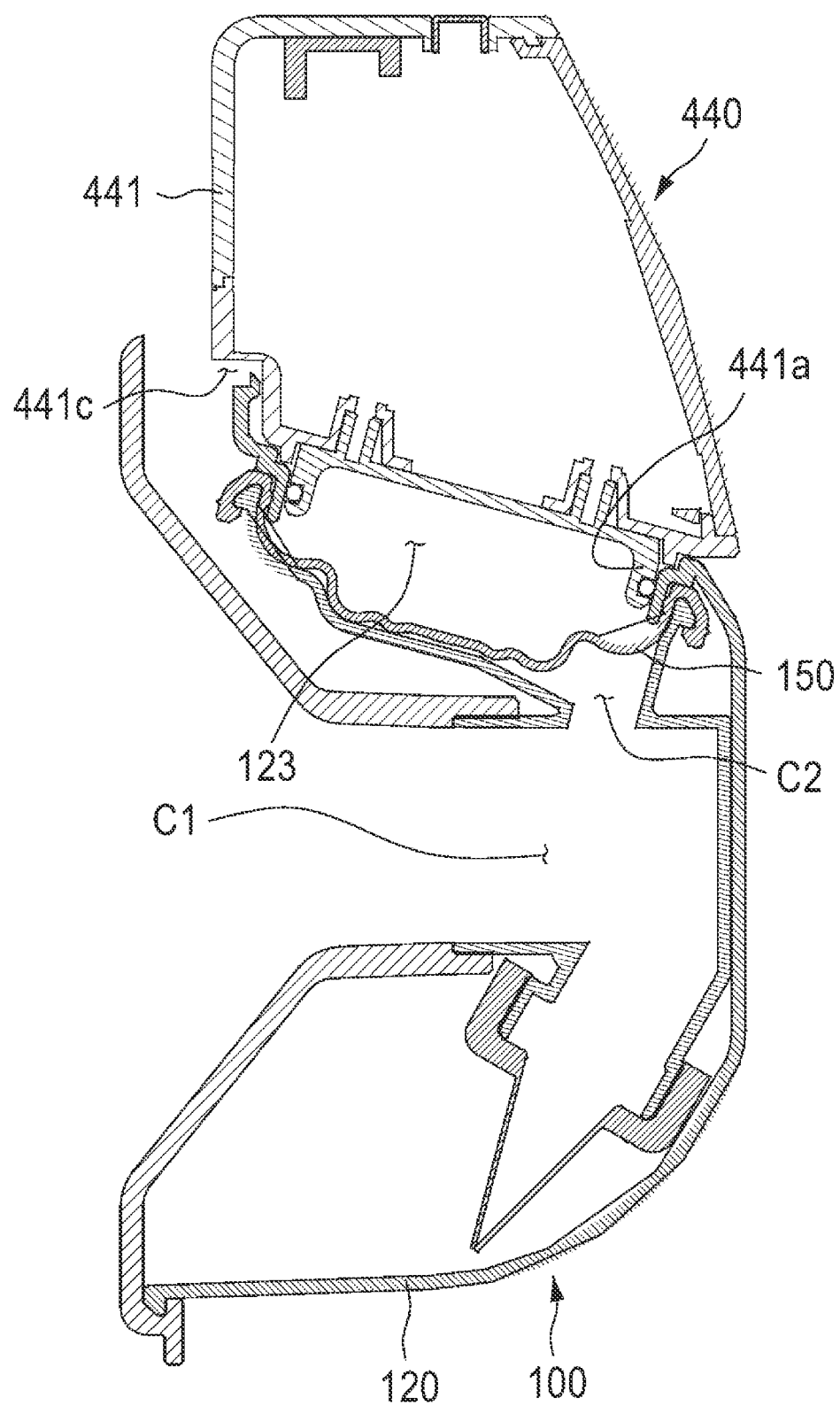
FIG. 9 is a cross-sectional view with the pump module shown in FIG. 5 coupled to the breast pump shown in FIG. 3.

FIG. 8 is a perspective view of the pump module shown in FIG. 5, and FIG. 9 is a cross-sectional view with the pump module shown in FIG. 5 coupled to the breast pump shown in FIG. 3. Referring to FIG. 8 and FIG. 9, the pump module 440 may be detachably coupled to the coupling cavity 123 of the breast pump 100 to close off an outlet of the coupling cavity 123. For example, an annular coupler 441a being fitted into the coupling cavity 123 may be formed at a bottom of the second case 441.

Moreover, the second case 441 may be provided with an air passage 441b penetrating the bottom of the second case 441. The air passage 441b may be disposed to connect to the coupling cavity 123 when the pump module 440 is coupled to the coupling cavity 123. For instance, the air passage 441b may be placed inside the annular coupler 441a. Moreover, the air passage 441b may be connected to the second milking pump 443 installed in the second case 441. As such, the second milking pump 443 may suck in the air of the coupling cavity 123 through the air passage 441b, and once the air of the coupling cavity 123 is discharged through the air passage 441b, the middle portion of the flow separation membrane 150 may move upwardly, thereby expanding the second inner space C2 to create a vacuum pressure within the second inner space C2. This vacuum pressure may be extended to the first inner space C1 to act as a force for extracting the breast milk from the breast of the lactating person.

The second case 441 may be additionally provided with a locking groove 441c and/or a USB socket 441d. The locking groove 441c may be in the form of, for example, a recess at a portion of an edge of a bottom face of the second case 441. The USB socket 441d may be connected to the second milking pump 420 or the second control panel 447 to transfer an external control signal required for driving the second milking pump 420 and may be connected to the second battery to charge the second battery with the power supplied from the external power source. The USB socket 441d may be in the form of, for example, a recess at a portion of the bottom face of the second case 441. Therefore, by keeping the USB socket 441d from protruding downwardly, the bottom face of the second case 441 may be in close contact with a flat top face of the storage housing 120, and thus the second case 441 may be securely supported on the storage housing 120.

Figure 10:
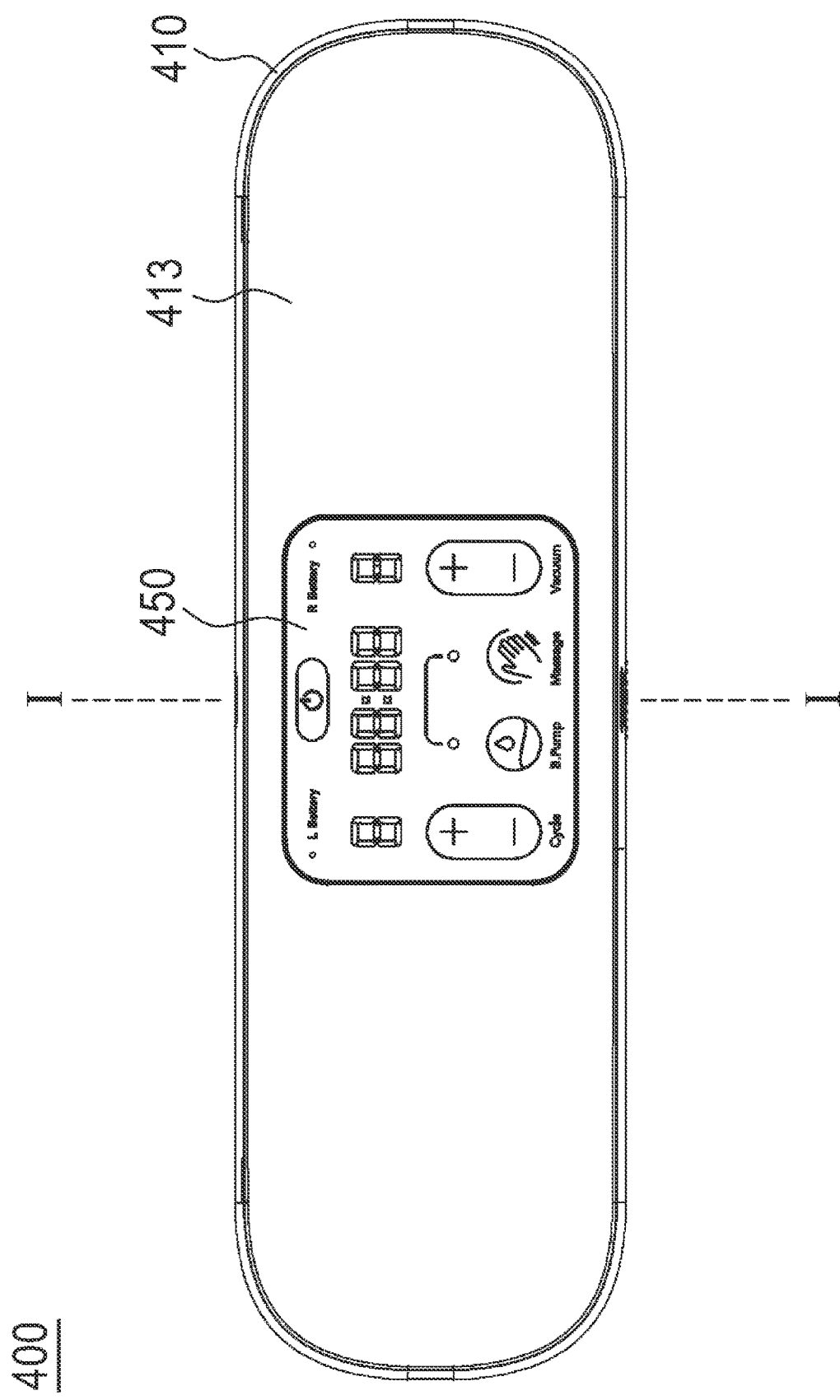
FIG. 10 is a top view of the pump cradle shown in FIG. 2.
Figure 11:
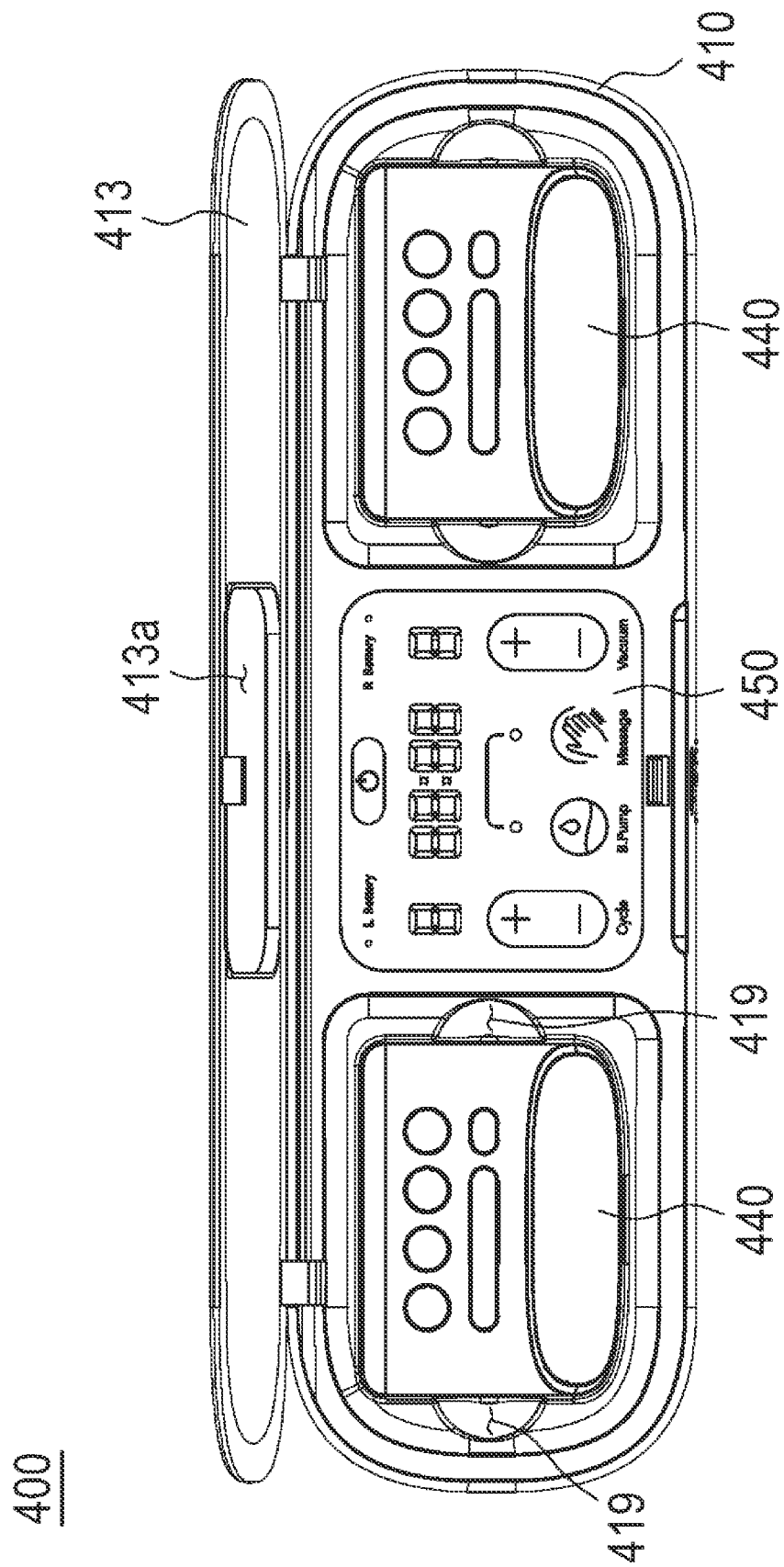
FIG. 11 is a top view illustrating the pump cradle of FIG. 10 with the cover opened.
Figure 12:
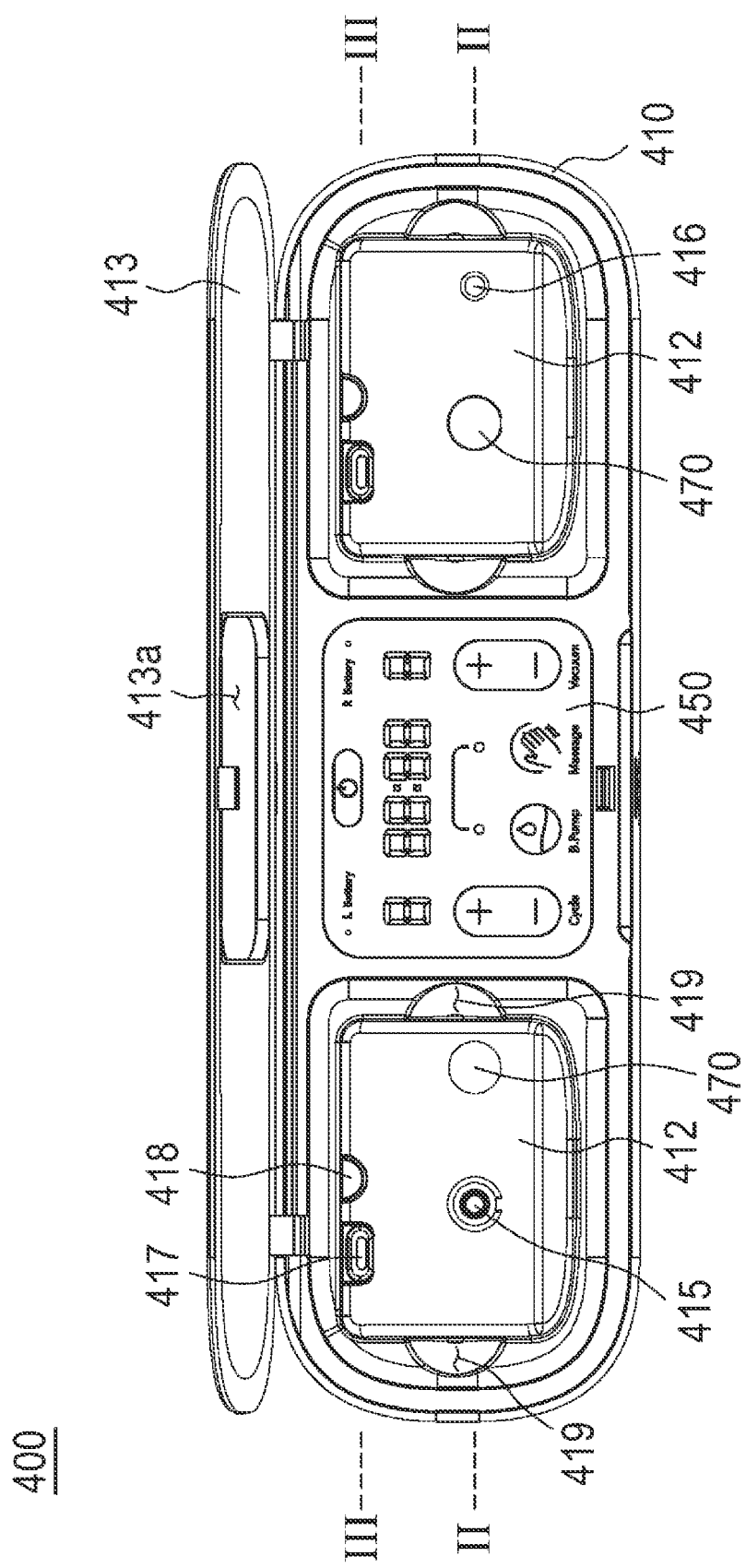
FIG. 12 is a top view of the pump cradle of FIG. 11 with the pump module removed.
Figure 13:
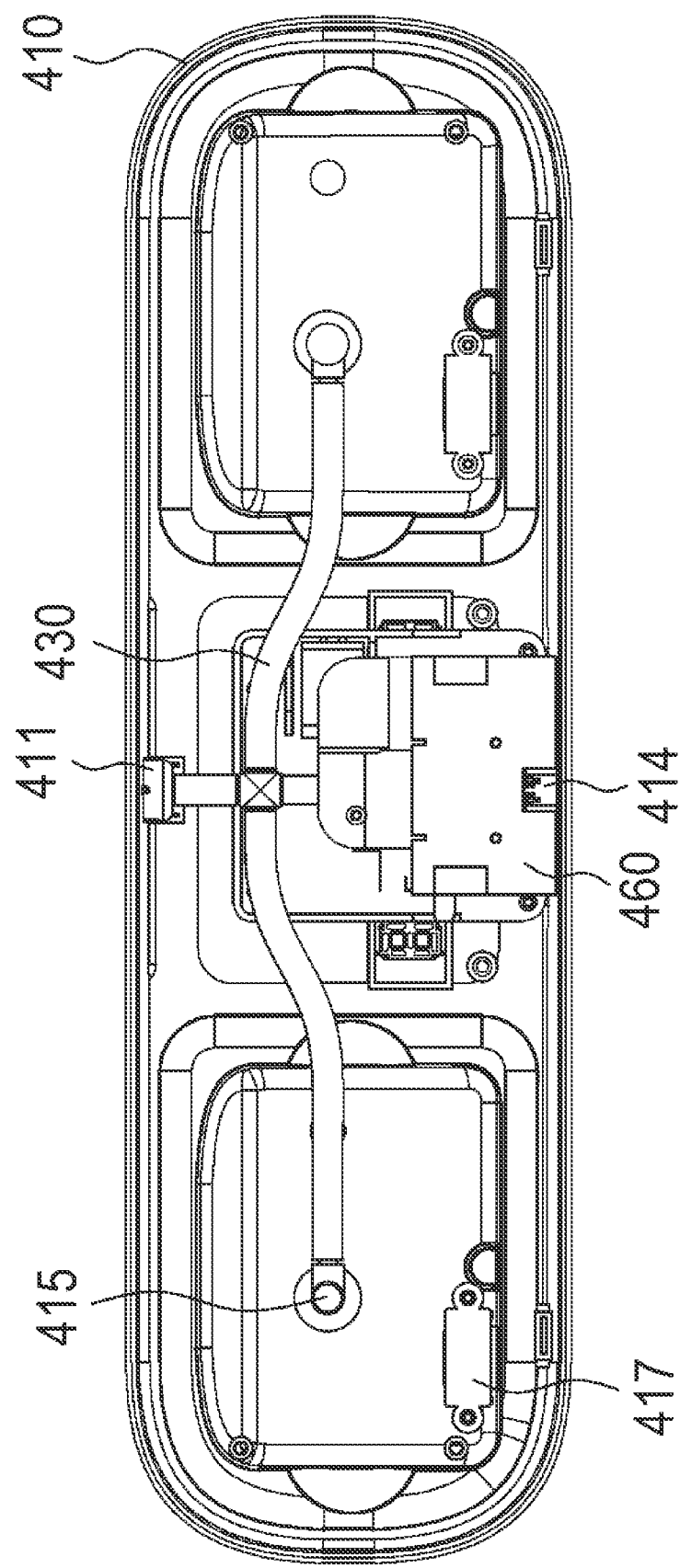
FIG. 13 is a bottom view illustrating an inside of the pump cradle shown in FIG. 10.
Figure 14:
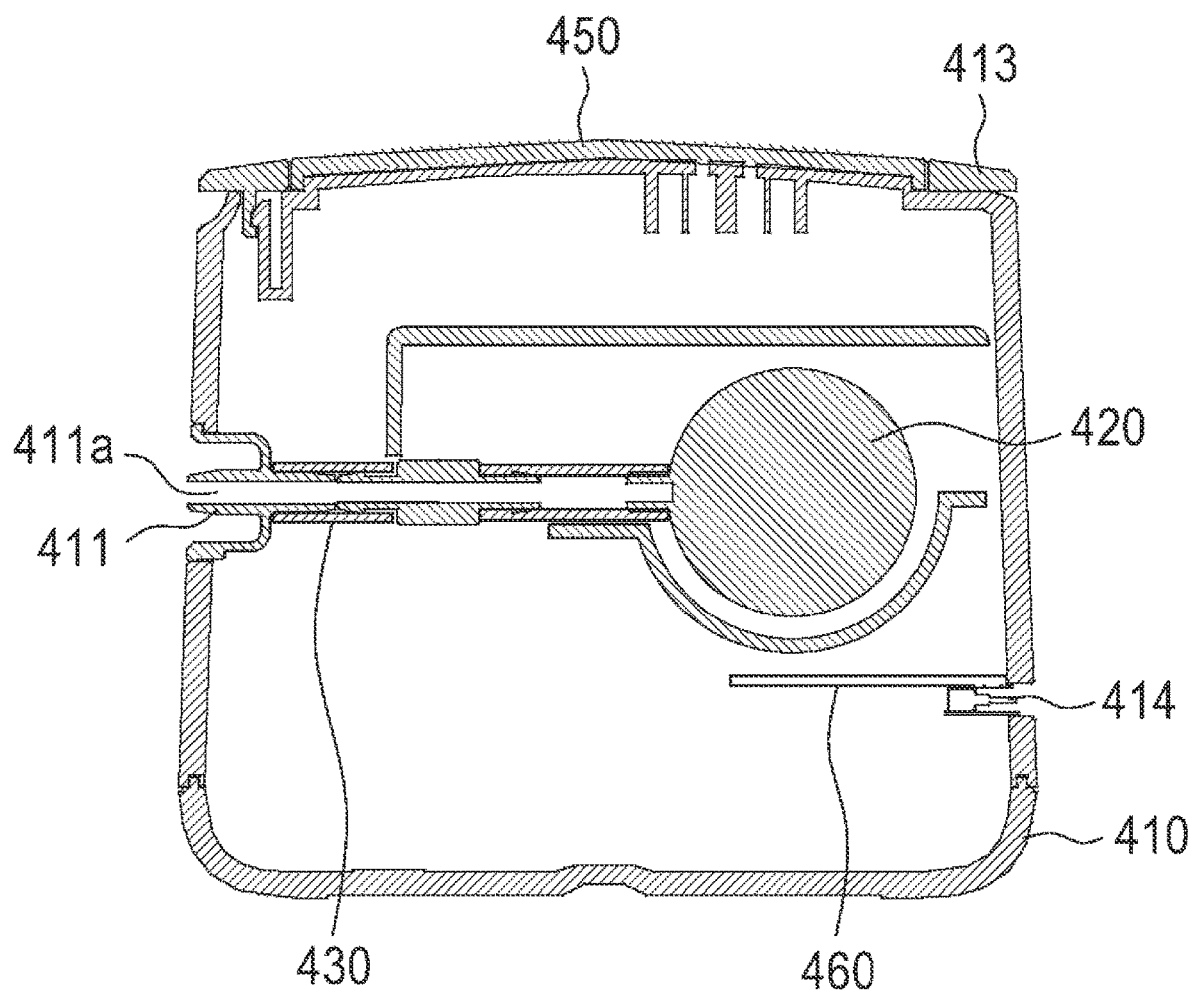
FIG. 14 is a cross-sectional view of FIG. 10 seen along the I-I line.
Figure 15:
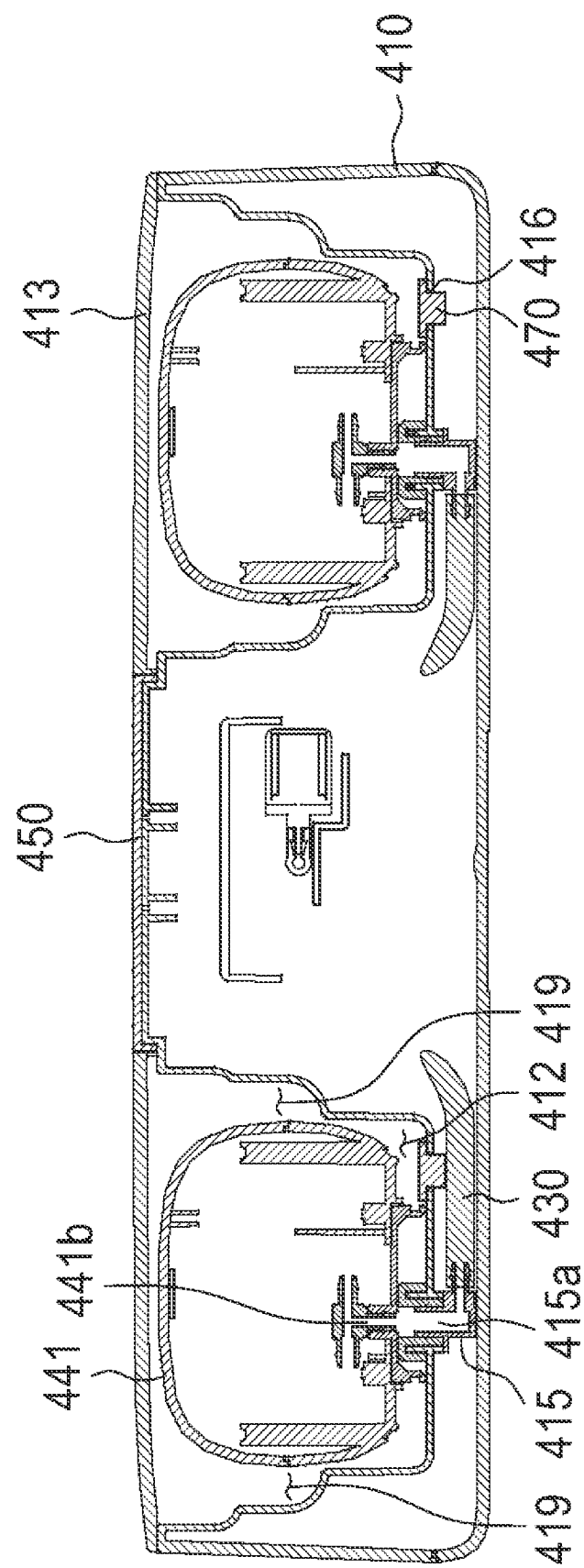
FIG. 15 is a cross-sectional view of the pump cradle of FIG. 10 seen along the II-II line shown in FIG. 12.
Figure 16:
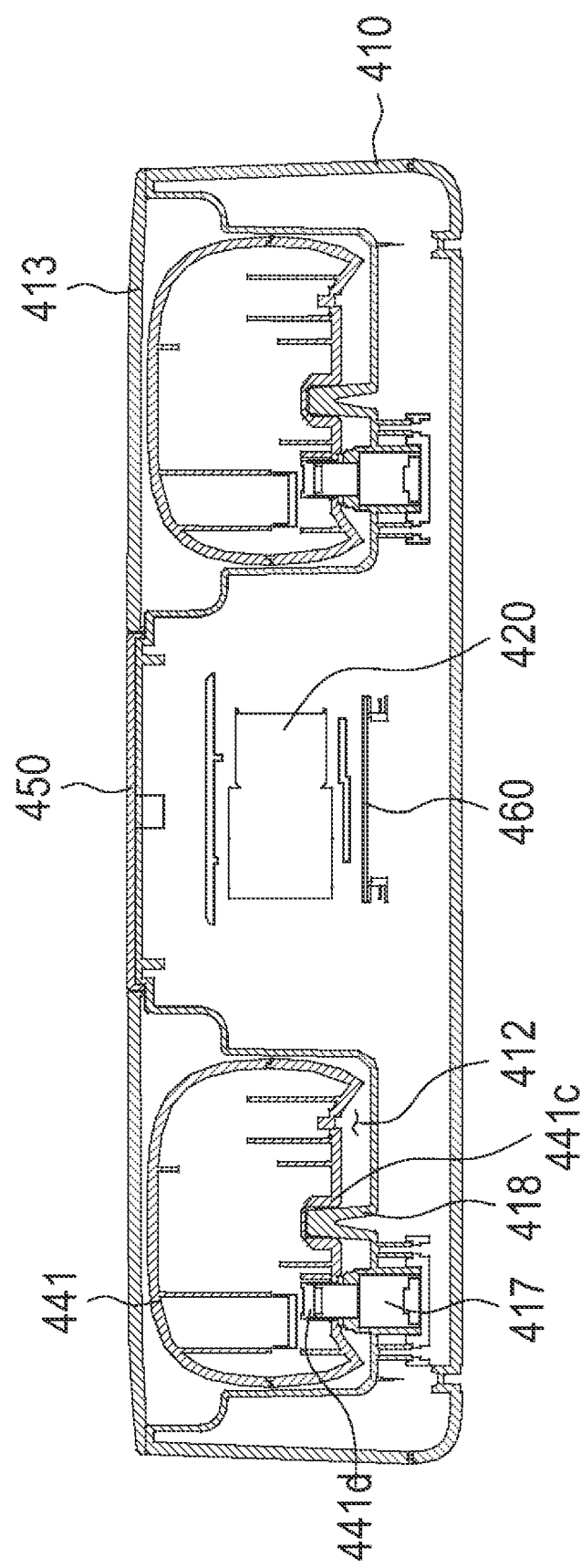
FIG. 16 is a cross-sectional view of the pump cradle of FIG. 10 seen along the III-III line shown in FIG. 12.

FIG. 10 is a top view of the pump cradle shown in FIG. 2; FIG. 11 is a top view illustrating the pump cradle of FIG. 10 with the cover opened; FIG. 12 is a top view of the pump cradle of FIG. 11 with the pump module removed; FIG. 13 is a bottom view illustrating an inside of the pump cradle shown in FIG. 10; FIG. 14 is a cross-sectional view of FIG. 10 seen along the I-I line; FIG. 15 is a cross-sectional view of the pump cradle of FIG. 10 seen along the II-II line shown in FIG. 12; and FIG. 16 is a cross-sectional view of the pump cradle of FIG. 10 seen along the III-III line shown in FIG. 12.

Referring to FIG. 10 to FIG. 16, the first case 410 may be provided with the second air pipe connector 411, the insertion hole 412 and an air passage connector 415, and may be additionally provided with the cover 413, the power socket 414, a receiving hole 416, a USB plug 417, a locking protrusion 418 and/or an insertion groove 419.

The second air pipe connector 411 may be connected to the first milking pump 420 and the air passage connector 415 via a duct 430 and may be provided with a second flow channel 411a connecting the inner space of the air pipe 300 with an inner space of the duct 430. The air passage connector 415 may be provided with a third flow channel 415a connected to the inner space of the duct 430. The air passage connector 415 may be in the form of a protrusion from a bottom surface of the insertion hole 412 and may be disposed such that the third flow channel 415a is connected to the air passage 441b of the pump module 440 when the pump module 440 is coupled to the insertion hole 412.

Accordingly, the air suction force of the first milking pump 420 may be extended to the air pipe 300 through the duct 430 and the second air pipe connector 411, and the air suction force of the second milking pump 443 may be extended to the air pipe 300 through the air passage 441b, the air passage connector 415, the duct 430 and the second air pipe connector 411, thereby expanding a maximum pumping capacity of the pump cradle 400 to a sum of a pumping capacity of the first milking pump 420 and a pumping capacity of the second milking pump 443.

In the case where some or all of the plurality of pump modules 440 are not coupled to the pump cradle 400 during the use, a sealing cap 470 may be coupled to the air passage connector 415. The sealing cap 470 may be detachably coupled to an upper end of the air passage connector 415 to close off the third flow channel 415a. Moreover, the sealing cap 470 may be stored in the receiving hole 416 provided in the first case 410 while not being used. This is for preventing the sealing cap 470 from being misplaced or lost. In an example, the receiving hole 416 may be formed in the bottom surface of the insertion hole 412, and the sealing cap 470 may be separated from the air passage connector 415 and detachably coupled to the receiving hole 416. Meanwhile, FIG. 12 illustrates both an example of the sealing cap 470 coupled to the air passage connector 415 (see the insertion hole 412 on the right side) and an example of the sealing cap 470 coupled to the receiving hole 416 (see the insertion hole 412 on the left side). The USB plug 417 may be in the form of, for example, a protrusion from the bottom surface of the insertion hole 412 to be detachably coupled to the USB socket 441d when the pump module 440 is coupled to the insertion hole 412. The USB plug 417 may be connected to the first control panel 460 via, for example, a wire or wires to transfer a control signal of the first control panel 460 to the USB socket 441d. Moreover, the USB plug 417 may be connected to the power socket 414 via, for example, the first control panel 460 to transfer the power from the external power source to the USB socket 441d. The power transferred from the external power source may be used for driving the second milking pump 443 or recharging the second battery.

The locking protrusion 418 may be in the form of, for example, a protrusion at an edge of the bottom surface of the insertion hole 412 to be detachably coupled to the locking groove 441c when the pump module 440 is coupled to the insertion hole 412. The locking protrusion 418 may align the pump module 440 and prevent the pump module 440 from moving within the insertion hole 412 by, for example, an external impact and the air suction force from leaking out.

The insertion groove 419 may be formed, for example, on two lateral faces of the insertion hole 412 that face each other and may extend vertically to be connected to the top face of the first case 410. Accordingly, the user may insert the fingers into the pair of insertion grooves 419 to grab the pump module 440, and as a result, the pump module 440 may be readily coupled to the first case 410 or removed from the first case 410.

Hitherto, a certain preferred embodiment has been described, but the present disclosure shall not be limited to the described embodiment. Anyone of ordinary skill in the art to which the present disclosure pertains will readily be able to modify or vary the described embodiment by means of supplementing, modifying, deleting or adding one or more elements of the present disclosure within the scope of the present disclosure, as defined by the appended claims, and such supplementation, modification, deletion or addition shall be deemed to be within the scope of the present disclosure.

DESCRIPTION OF REFERENCE NUMERALS

10: breast pump assembly
110: contact housing
111a: breast milk inflow cavity
100: breast pump
111: backside
113: frontside
113a: protruding part
121: breast milk outflow cavity
130: cap connector
133: silicon valve
150: flow separation membrane
210: first air pipe connector
300: air pipe
410: first case
411a: second flow channel
413: cover
414: power socket
415a: third flow channel
417: USB plug
419: insertion groove
430: duct
441: second case
441b: air passage
441d: USB socket
445: second input unit
450: first input unit
470: sealing cap
120: storage housing
123: coupling cavity
131: breast milk outflow tube
140: funnel connector
200: stopper
210a: first flow channel
400: pump cradle
411: second air pipe connector
412: insertion hole
413a: through hole
415: air passage connector
416: receiving hole
418: locking protrusion
420: first milking pump
440: pump module
441a: coupler
441c: locking groove
443: second milking pump
447: second control panel
460: first control panel

What is claimed is:

1. A breast pump assembly, comprising:
a breast pump comprising: a contact housing with a backside recessed to wrap a breast; and a storage housing coupled to the contact housing to define a breast milk storage space on a frontside of the contact housing, the breast pump being provided with a coupling cavity penetrating an upper portion of the storage housing;
a stopper detachably coupled to the coupling cavity and provided with a first air pipe connector;
an air pipe coupled to the first air pipe connector; and
a pump cradle provided with a second air pipe connector to which the air pipe is coupled,
wherein the pump cradle comprises:
a first case provided with the second air pipe connector, an insertion hole and an air passage connector;
a first milking pump installed in the first case;
a duct connecting the first milking pump and the air passage connector to the second air pipe connector; and
a pump module comprising a second case detachably coupled to the insertion hole and a second milking pump installed in the second case,
wherein the second case is provided with an air passage connecting the air passage connector with the second milking pump, and
wherein the pump module is configured to be separated from the insertion hole and detachably coupled to the coupling cavity when the stopper is separated from the coupling cavity.

2. The breast pump assembly according to claim 1, wherein the air passage is connected to the coupling cavity when the pump module is coupled to the coupling cavity.

3. The breast pump assembly according to claim 1, wherein the pump cradle further comprises:
a first input unit; and
a first control panel configured for driving the first milking pump and the second milking pump based on an actuating signal inputted through the first input unit.

4. The breast pump assembly according to claim 3, wherein the second milking pump is connected to the first control panel through a Universal Serial Bus (USB) plug and a USB socket provided in the first case and the second case, respectively, and detachably coupled with each other.

5. The breast pump assembly according to claim 3, wherein the pump module further comprises:
- a second input unit; and
- a second control panel configured for driving the second milking pump based on an actuating signal inputted through the second input unit.

6. The breast pump assembly according to claim 5, wherein the first input unit is coupled to the first case, and the second input unit is coupled to the second case.

7. The breast pump assembly according to claim 1, wherein the pump cradle further comprises a sealing cap detachably coupled to the air passage connector when the air passage connector is separated from the air passage, and wherein the first case is provided with a receiving hole, the sealing cap being configured to be separated from the air passage connector and detachably coupled to the receiving hole.

8. The breast pump assembly according to claim 1, wherein the contact housing is provided with a protruding part configured to receive a nipple of the breast and extending toward a front of the contact housing, and
wherein the breast pump further comprises:
- a cap connector coupled to the protruding part and forming a first inner space being connected to the backside;
- a funnel connector coupled to the cap connector and forming a second inner space being connected to the first inner space; and
- a flow separation membrane configured to separate the second inner space from the coupling cavity.

9. The breast pump assembly according to claim 8, wherein the cap connector is provided with a breast milk outflow tube connecting the first inner space with the breast milk storage space.

10. A pump cradle for a breast pump, comprising:
- a first case provided with an air pipe connector, an insertion hole and an air passage connector, the air pipe connector being configured to be connected to the breast pump through an air pipe;
- a first milking pump installed in the first case;
- a duct connecting the first milking pump and the air passage connector to the air pipe connector;
- a pump module comprising a second case detachably coupled to the insertion hole and a second milking pump installed in the second case;
- a first input unit; and
- a first control panel configured for driving the first milking pump and the second milking pump based on an actuating signal inputted through the first input unit while the pump module is coupled to the insert hole,
wherein the second case is provided with an air passage connecting the air passage connector with the second milking pump, and
wherein the pump module is configured to be separated from the insertion hole and configured to be detachably coupled to the breast pump.

* * * * *